United States Patent [19]

Naveh et al.

[11] Patent Number: 5,034,133
[45] Date of Patent: Jul. 23, 1991

[54] PURIFICATION OF HUMAN INTERLEUKIN-4 FROM A CHO-CELL LINE CULTURE MEDIUM

[75] Inventors: David Naveh, Leiden, Netherlands; Jay Raman, Robinsville; John C. T. Tang, Livingston, both of N.J.

[73] Assignee: Schering-Corporation, Kenilworth, N.J.

[21] Appl. No.: 558,139

[22] Filed: Jul. 26, 1990

[51] Int. Cl.$^5$ .............................................. B01D 15/08
[52] U.S. Cl. .................................. 210/635; 210/656; 514/2; 530/351; 530/413; 530/416; 530/417
[58] Field of Search ..................... 210/635, 656; 514/2; 530/351, 413, 416, 412, 417

[56] References Cited

U.S. PATENT DOCUMENTS

| | | | |
|---|---|---|---|
| 4,440,675 | 4/1984 | Braude | 530/351 |
| 4,541,952 | 9/1985 | Hosoi | 530/351 |
| 4,551,271 | 11/1985 | Hochuli | 530/351 |
| 4,658,017 | 4/1987 | Dembinski | 530/351 |
| 4,732,683 | 3/1988 | Georgiades | 210/635 |
| 4,765,903 | 8/1988 | D'Andrea | 210/635 |
| 4,894,330 | 1/1990 | Hershenson | 530/351 |
| 4,958,007 | 9/1990 | Alroy | 530/351 |
| 4,959,455 | 9/1990 | Clark | 530/351 |
| 4,965,195 | 10/1990 | Namen | 530/351 |

OTHER PUBLICATIONS

Yokota, et al., Isolation and Chartacterization of Human Interleukin c DNA clone Proc. Natl. Acad. Sci, U.S.A. 83 5894–98 )1986).
Lee, et al., Isolation and Characterization of Mouse Interleukin c DNA clone Proc. Natl. Acad. Sci., U.S.A., 83 2061–65 (1986).
Noma, et al., Cloning CDNA encoding the Murine IGGL Induction Factor Nature, 319, 640–46 (1986).

*Primary Examiner*—Ernest G. Therkorn
*Attorney, Agent, or Firm*—Norman C. Dulak; James R. Nelson; Gerald S. Rosen

[57] ABSTRACT

Active recombinant human IL-4 is purified from a crude cell culture medium of a CHO-cell lines mutant by subjecting said crude solution to two sequentialcation exchange chromatographies at pH 7.2 and 0.12M sodium chloride, selective chromatography on a cobalt-chelating agarose column at pH 7.2 in a buffer containing a high concentration of sodium chloride, i.e., about 0.5M sodium chloride, further treated by concentration (diafiltration) up to 20 mg/mL and size exclusion gel chromatography using a citrate buffer at pH 4.5.

7 Claims, No Drawings

PURIFICATION OF HUMAN INTERLEUKIN-4 FROM A CHO-CELL LINE CULTURE MEDIUM

FIELD OF INVENTION

This invention relates generally to a method for purifying soluble active human interleukin-4 expressed in certain Chinese Hamster Ovary (CHO) cell lines.

BACKGROUND

Human interleukin-4 (IL-4) is a natural protein which is believed to have a therapeutic potential against infection, cancer and autoimmune disease and was characterized by Yokota et al., Proc. Natl. Acad. Sci., USA, 83, 5894–5898 (1986). Mouse IL-4 is reported by Lee, et al., Proc. Natl. Acad. Sci. USA, 83, 2061–2065 (1986) and Noma, et al. Nature, 319, 640–646 (1986).

In the production of genetically engineered IL-4, separation of the expressed protein from the transformed host cells or their cultures supernatants can be a major problem, Dwyer, Biotechnology, 2, 957 (1984).

Clinical use of active IL-4 requires a high purity material that is not contaminated by cell constituents or cell debris of the IL-4 expressing cell. Accordingly, purification of active IL-4 in the cell culture medium of IL-4 expressing CHO-cell lines in high yields and high purity is needed.

This invention relates to purifying active soluble IL-4 resulting from its expression in certain CHO-cell lines.

SUMMARY OF THE INVENTION

The present invention is based on the discovery that high purity active IL-4 can be obtained from the cell culture medium of IL-4 expressing CHO-cell lines in a process comprising:

1. Subjecting crude cell culture medium containing active IL-4 to cation exchange chromatography on a S-Sepharose® Fast Flow column at a near neutral pH of about 6.7 to 8, preferably 7.2, and at 13–15 mS (conductivity) where most impurities do not bind. S-Sepharose®, Fast Flow available from Pharmacia Fine Chemicals, Piscataway, N.J. is a cross-linked agarose matrix having coupled thereto the ion exchange group $-CH_2-SO_3-$ $Na^+$. The column is washed with equilibration buffer then the purified IL-4 in a buffered solution is isocratically eluted from the column by a buffer system at pH 7.2, containing 0.26M NaCl and pooled;

2. Subjecting the pooled eluate from step 1 to further cation exchange chromatography on a relatively small S-Sepharose® Fast Flow column which is about 15% the bed volume of the column of step 1. The column is washed with an equilibration buffer, then the active IL-4 molecule is eluted by a buffer system at pH 7.2 containing a sodium chloride gradient 0.12–0.50M;

3. Subjecting the solution of active IL-4 from step 2 to affinity chromatography on a metal chelating-agarose gel column after adjusting the solution to pH 7.2 and conductivity to 45–50 mS. The chelating-Sepharose® gel is available from Pharmacia Fine Chemicals, Piscataway, N.J. under the names chelating-Sepharose® Fast Flow and chelating-Sepharose® 6B. Chelating Sepharose® Fast Flow consists of iminodiacetic acid groups on spacers coupled to Sepharose® 6 Fast Flow by stable ether linkages. Sepharose® 6 Fast Flow is a crosslinked agarose, 6%. A buffer, preferably a phosphate buffer, is used. The phosphate buffer used is one with a sodium chloride concentration of about 0.5M at a neutral to slightly alkaline pH, i.e. about pH 6.7–8, preferably about 7.2. The salt concentration and near neutral pH of about 7.2 helps maximize binding of the active interleukin-4 and minimize binding of other proteins to the column. The preferred metal chelate is cobalt although other metal chelates such as zinc, copper or nickel can be used. After the binding is completed, the column is washed with an equilibration buffer containing 20 mM sodium phosphate, pH 7.2 and 0.5M sodium chloride. Finally, the active IL-4 is isocratically eluted at pH 6.0 with a phosphate buffer containing 0.50M sodium chloride;

4. Subjecting the active IL-4 solution to gel filtration chromatography on a size exclusion column, preferably Sephacryl® S-200 HR or S-100 HR which are crosslinked copolymers of allyldextran and N,N'-methylene bisacrylamide which are available from Pharmacia, equilibrated with 10 mM sodium citrate, pH 4.5 after concentration up to 20 mg/mL at pH 4.5. Then collecting the purified active IL-4 solution which is 95%-99% pure.

As used herein "active IL-4" means soluble undenatured recombinant human IL-4 in its natural biologically active conformation.

DETAILED DESCRIPTION

The method of this invention makes it possible to subject a crude solution of active recombinant human interleukin 4 to cation exchange chromatography, metal chelating affinity chromatography, and size exclusion chromatography to obtain high purity active IL-4. The sequential order of the chromatography steps is critical to the process of this invention because the degree of purity achieved in the cation exchange chromatography, i.e. about 60–70%, enables the remaining chromatography steps to efficiently remove closely related, hard to separate impurities.

The cation exchange chromatography is carried out in two steps after the CHO-cell culture medium is filtered to remove extraneous large cell debris, then concentrated to up to 100 mg/mL protein on a diafiltration membrane and the pH is adjusted to pH 7.1–7.3, preferably 7.2. The membrane is preferably a stirred cell fitted with a membrane which holds all material greater than 10,000 MW, e.g. a YM-10 membrane, Amicon Co., U.S.A., or Pellicon filter PTGC Cassettes, Millipore Corp., Bradford, Mass. In the first step, crude culture medium is loaded on a cation exchange chromatography column such as S-Sepharose® Fast Flow (up to 100 mg protein per ml resin) previously equlibrated with a phosphate buffer of near neutral to slightly alkaline pH, i.e. pH 6.7–8, preferably 7.2, containing 0.12M sodium chloride. This results in the active IL-4 remaining on the column and most undesired proteins and other impurities being washed through. The active IL-4 is then isocratically eluted from the column with a sodium phosphate buffer, preferably one of pH 7.1–7.3, more particularly, pH 7.2, with 20 mM sodium phosphate and about 0.26M sodium chloride. The fractions containing active IL-4 as determined by the SDS-PAGE and protein assays are pooled and the pool is adjusted to pH 7.2 and 14 mS.

In the second step, the adjusted pool from the first step is loaded on a relatively small cation exchange chromatography column, about 15% bed volume of the cation exchange column used in step 1, equilibrated with a phosphate buffer, impurities are washed through, and the active IL-4 remains on the column. The active IL-4 is eluted with a sodium chloride gradient of 1.75 mS per bed volume. The eluting buffers consist of a low salt buffer, i.e. 20 mM sodium phosphate, pH 7.2, 0.12M sodium chloride and a high salt buffer, i.e. 20 mM sodium phosphate, pH 7.2, 0.50M sodium chloride. The gradient fractions containing the active IL-4 as determined by SDS-PAGE and protein assays are pooled and adjusted to pH 7.2 and 45–50 mS.

The pool of active IL-4 fractions from the cation exchange chromatography which is about 60–70% pure is then subjected to affinity chromatography on a metal chelating agarose gel column prepared by metal treated chelating-Sepharose ® gel, i.e. chelating-Sepharose ® Fast Flow or chelating-Sepharose ®6B. The chelating columns comprise two portions in a single column. The top part of the column contains a metal treated-chelating agarose gel, preferably a cobalt treated-chelating-Sepharose ®Fast Flow gel, and the bottom part of the column is an untreated chelating-Sepharose ®Fast Flow gel. The volume ratio of the two layers is about 2.3–3.0 volumes of cobalt treated-chelating Sepharose ® to one volume of untreated chelating Sepharose ®. When the pool of purified IL-4 from the cation exchange treatment is loaded unto the top of the column, the solution flowing through traverses to the bottom portion of the column where the flow-through containing any remaining impurities exits.

By using a buffer at near neutral, preferably pH 7.2, and preferably about 0.5M sodium chloride, active IL-4 molecules are selectively bound by affinity chromatography to a metal chelating-agarose gel column, preferably chelating Sepharose ® Fast Flow or Sepharose ® 6B, to the substantial exclusion of contaminating proteins present in the solution. The active IL-4 remains on the columns and is isocratically eluted with a buffer at a slightly acid pH, preferably at pH 6.0 containing 0.5M NaCl.

The purified solution of active IL-4 from the affinity chromatography column is concentrared on an ultrafiltration membrane (10,000 MW cut-off), preferably on a stirred cell fitted with a membrane which holds all material with greater than 10,000 molecular weight, which range includes IL-4. A preferred membrane is YM-10 manufactured by Amicon Co., USA. The concentration obtained is up to 20 mg/mL. Two diafiltration buffers are used, first a 20 mM Na-phosphate buffer at pH 6.0 with 0.05M EDTA and 0.5M sodium chloride, and a second buffer which is preferably 10 mM sodium citrate at pH 4.5.

The concentrated eluates of active IL-4 are charged to a size exclusion gel filtration column which fractionates the proteins in the solution according to molecular weight. A typical column which is suitable is a Sephacryl ®S-200 HR or S-100 HR (Pharmacia) gel filtration column. The Sephacryl ®S-200 HR (high resolution) and S-100 HR are crosslinked copolymers of allyldextran and N,N'-methylene bisacrylamide. Their fractionation range in Daltons is 5,000–250,000 and 1,000–100,000, respectively. Other suitable materials are the Sephadexes ® (Pharmacia) which are crosslinked dextran gels. Preferably, the solution of active IL-4 is charged to an S-200 HR column previously equilibrated with a 10 mM citrate buffer at pH 4.5

The source of the crude solution of active IL-4 according to the process of this invention is the cell culture medium containing secreted therein active human IL-4 expressed by certain CHO-cell lines.

Thus the invention is a process for purifying a crude solution of active recombinant human IL-4 comprising.

(a) subjecting a buffered crude solution of active IL-4 from a CHO-cell culture medium to cation exchange chromatography at a near neutral to a slightly alkaline pH to selectively bind the IL-4, and isocratically eluting the IL-4;

(b) subjecting the eluate from step (a) to further cation exchange chromatography on a relatively small column (15% bed volume of the column used in step (a)) at a near neutral to slightly alkaline pH and gradient eluting the IL-4;

(c) subjecting the eluate from step (b) to affinity chromatography on a chelating agarose gel column system at a near neutral to slightly alkaline pH, then eluting the IL-4 with an acidic buffer;

(d) concentrating the eluate from step (c) with an ultrafiltration membrane (10,000 molecular weight cut-off); and (e) subjecting the concentrated solution of active IL-4 from step (d) to gel filtration chromatography on a size exclusion column at an acid pH and collecting the purified IL-4 solution.

The process of this invention in a more preferred embodiment comprises:

(a) subjecting a crude buffered solution of active recombinant human IL-4 from a CHO-cell cell culture medium to cation exchange chromatography on a cross-linked agarose column (preferably S-Sepharose ®Fast Flow) in a 20 mM phosphate buffer, pH 6.7 to 8, preferably, pH 7.2, with 0.12M sodium chloride at 13–15 mS, preferably 14 mS, then isocratically eluting the active IL-4 from the column with a 20 mM phosphate buffer at pH 7.1 to 7.3, preferably, pH 7.2 with 0.26M sodium chloride and collecting the active IL-4 fractions;

(b) subjecting the IL-4 solution from step (a) to additional cation exchange chromatography on the same type of cross-linked agarose column used in step (a) but having a bed volume of about 15% of the column used in step (a), in a buffer at pH 7.2–7.5, preferably 7.2, containing 0.12M sodium chloride, then gradient eluting with a 20 mM phosphate buffer at pH 7.2 containing 0.12M to 0.50M sodium chloride and pooling the fractions containing active IL-4;

(c) subjecting the pooled fractions of active IL-4 from step (b) at pH 7.2 to affinity chromatography on a metal chelating agarose gel column, preferably consisting of a top portion of a cobalt-chelating Sepharose ®Fast Flow or 6B gel and a bottom portion of untreated chelating Sepharose ®Fast Flow gel, with a 20 mM phosphate buffer at pH 7.2 containing 0.5M sodium chloride, the volume ratio of the two portions is about 2.3–3.0 volume of cobalt-treated chelating Sepharose ® to one volume of untreated chelating Sepharose ® washing with an equilibration buffer, then eluting the active IL-4 with a phosphate buffer at pH 6.0 containing 0.5M sodium chloride and collecting the IL-4 fractions; and (d) concentrating and diafiltering the IL-4 fractions (pooled) from step (c) to up to 20 mg/mL at pH 4.5 on an ultrafiltration membrane which holds all material with greater than 10,000 molecular weight, preferably a stirred cell fitted with a membrane such as YM-10, then subjecting the active IL-4 concentrate to size exclusion (gel filtration) chromatography on a column which fractionates the proteins in the solution according to molecular weight on a cross-linked copolymers of allyldextran and N,N'-methylene bisacrylamide, preferably Sephacryl®S-200 HR in a 10 mM sodium citrate buffer at pH 4.5 and collecting the active IL-4 fractions.

In step (a) the crude solution charged to the cation exchange column in the preferred practice of this invention is from CHO-cell cell culture medium which had been previously treated to remove cell debris and other large particles which result from cell culture processes. More particularly, the process of this invention is applicable to purification of active IL-4 which is produced by CHO-cell mutants which are genetically engineered to produce active human IL-4 and secrete the active human IL-4 into the culture medium.

Preferably the active human IL-4 is produced by CHO-cell mutants deficient in dihydrofolate reductase activity into which an expression vector with the human IL-4 cDNA sequence is incorporated.

Preferably the IL-4 is produced by a CHO-cell lines mutant as described in applicants assignees' pending U.S. patent application Ser. No. 386,937, filed July 25, 1989, which application is incorporated in its entirety by reference herein. Of particular relevance are pages 20 and 21 which describe the construction of the human IL-4 expression plasmid pdhfr-SRalpha263 which has been described in the literature noted in the patent application. Pages 21-24 describe the preparation of active human IL-4 using the preferred CHO-cell clone 3B12-A26-19.

The IL-4 prepared as disclosed in the referenced patent application is purified by filtering, concentration, cation exchange chromatography, metal chelate affinity chromatography, concentration and gel filtration chromatography.

In step (a) and step (b) the pH of the fractions are adjusted to pH 7.2 and a conductivity of 13-15 mS with 4M NaCl. The bed volume ratio of the two cation exchange columns is about 6.3 volume of S-Sepharose® column in step (a) and one volume of the cation exchange column in step (b). The cation exchange gel material in a chromatography column is equilibrated with a 20 mM phosphate buffer at pH 7.2 having 0.12M sodium chloride. A preferred cation exchanger is crosslinked agarose substituted with —$CH_2$—$SO_3$— Na+ groups, such as S-Sepharose® Fast Flow available from Pharmacia. The active IL-4 is isocratically eluted in step (a) with a 20 mM phosphate buffer at pH 7.2 with 0.26M NaCl. The fractions with highest concentrations of active IL-4 based on the SDS-PAGE and protein assays are pooled. The pooled fractions solution is adjusted to pH 7.2 and the conductivity is adjusted 13-15 mS per bed volume with 20 mM sodium phosphate buffer pH 7.2 The column is then loaded with the IL-4 solution and gradient eluted using a gradient of 1.75 mS per bed volume with 20 mM sodium phosphate buffers of pH 7.2 containing 0.12-0.50M NaCl. The collected IL-4 containing fractions as determined by the SDS-PAGE and protein assays are pooled. The conditions for cation exchange chromatography are selected to insure that the active IL-4 fraction will attach to the cation exchanger matrix. The near neutral pH 7.2 which is relatively high for a cation exchange chromatography and the 13-15 mS conductivity which is relatively high for an ion exchange chromatography results in mild binding conditions where most impurities do not bind to the column, elution is relatively easy and high purity of the active IL-4 solution is obtained, i.e. about 60%-70%.

The preferred metal chelating-agarose utilized in step (c) is chelating Sepharose® Fast Flow, although chelating Sepharose®6B is also satisfactory. The Sepharoses are products of Pharmacia Fine Chemicals, Piscataway, N.J. A preferred method of preparing the preferred cobalt chelating Sepharose® column for use in this invention is by suspending the Sepharose® gel in 0.02M cobalt acetate solution and wash with deionized water, then an equilibration buffer, i.e. 20 mM sodium phosphate, pH 7.2, 0.5M NaCl solution through the column. Instead of cobalt acetate, other cobalt salts may be used, e.g. cobalt chloride or cobalt sulfate.

The chromatography column comprises one column containing two layers, the first or top layer contains a metal chelating-Sepharose® gel and the second or bottom layer contains chelating Sepharose® gel which has not been treated with a metal salt. The volume ratio in the dual columns is about 2.3 to 3.0 volumes of metal treated chelating Sepharose® to one volume of untreated chelating Sepharose®. The preferred metal is cobalt.

The preferred buffer used to equilibrate the columns is a 0.02M phosphate buffer at pH 7.2-7.5 containing 0.5M sodium chloride.

In step (c) the cobalt chelating-Sepharose® and the untreated chelating Sepharose® gels are equilibrated with a phosphate buffer at pH 7.2 containing 0.5M sodium chloride, then the adsorbed active IL-4 is isocratically eluted from the cobalt chelating-Sepharose® through the untreated chelating-Sepharose® with a 0.02M phosphate buffer at pH 6.0 with 0.5M sodium chloride or alternatively with a neutral pH buffer containing a 0.5M NaCl and of (i) a chelating agent such as 50 mM EDTA (ethylenediaminetetraacetic acid), or (ii) an analog of histidine such as 50 mM imidazole, or (iii) an amino acid such as 50 mM histidine. Preferred is the phosphate buffer at pH 6.0 with 0.5M NaCl. The eluate containing active IL-4 is collected. The fractions with the highest concentrations of active IL-4 based on the conventional SDS-PAGE and protein assays are pooled.

In step (d) the pooled eluted fractions from step (c) are concentrated and diafiltered then subjected to gel filtration chromatography. The eluted fractions are concentrated on a stirred cell fitted with a membrane which holds all material with greater than 10,000 molecular weight and diafiltered first against a 0.02M sodium phosphate buffer, pH 6.0 containing 0.05M EDTA (ethylene diamine tetraacetic acid) and 0.5M NaCl, then 0.01M sodium citrate, at pH 4.5. Since, at this stage of the process the active IL-4 solution is about 90-95% pure, that is in the concentrated solution retained on top of the membrane. A preferred membrane is YM-10 manufactured by Amicon Co., U.S.A. The concentration obtained is up to about 20 mg/mL of active IL-4. The concentrated eluates of active IL-4 are charged to a size exclusion (gel filtration) column which fractionates proteins in the solution according to molecular weight. A typical column which is suitable is a Sephacryl®S-200 HR or S-100 HR (Pharmacia) gel filtration column. The Sephacryl®S-200 HR (high resolution) and S-100 HR are crosslinked copolymers of allyldextran and N,N'-methylene bisacrylamide. Their fractionation ranges are 5,000-250,000 and 1,000-100,000, respectively. Other suitable materials are the Sephadexes® (Pharmacia) which are crosslinked dextran gels. Preferably the solution of active IL-4 is charged to an S-200 HR column previously equilibrated with a 10 mM sodium citrate buffer at pH 4.5. Under the conditions of step (d) the stable IL-4 concentrate can reach up to 20 mg/ml. This increases the capacity and performance of the gel filtration chromatography. The fractions of eluate containing the highest concentrations of active IL-4 as determined by the SDS-PAGE and protein assay are collected and pooled to result in a 95-99% pure solution of active IL-4.

Although any solubilized biologically active impure recombinant human interleukin-4 can be purified according to the process of this invention, most practically, the process of this invention is applicable to recombinant human active IL-4 produced by a CHO-cell line which secretes active IL-4 into the culture medium.

In its preferred embodiment, the process of this invention provides for purification of active human IL-4 produced by CHO-cell lines genetically engineered to produce active human IL-4 and excrete it into solution in the cell culture medium.

The preferred CHO-cell line used to prepare the active IL-4 purified according to the preferred embodiment of this invention is, as indicated supra, CHO-cell clone 3B12-A26-19.

Recovery of the active IL-4 from the culture medium is preferably carried out by centrifuging the culture medium or by microfiltration to remove cell debris and other relatively large particles. The resulting solution is then subjected to ultrafiltration on a filter such as a YM-10 membrane or Pellicon filter PTGC cassettes (Millipore Corp., Bedford, Mass.) which retains proteins having molecular weight greater than 10,000. The retentate, which is a concentrated crude solution of active IL-4 is diafiltered with 20 mM phosphate buffer at pH 7.2 containing 0.12M NaCl.

The thus treated crude solution of IL-4 is then purified as described above.

The buffers utilized in the process of this invention are chosen because they provide the proper conditions of binding, washing and elution to enable the active IL-4 either to adsorb to the chromatography gels or elute selectively therethrough. The preferred buffers are sodium phosphate buffers at a concentration of 20 mM or sodium citrate buffers at a concentration of 10 mM and pHs as shown in the examples, as well as the specific amount of sodium chloride indicated. The pH is adjusted with sodium hydroxide or acid.

The concentration of the sodium chloride in the buffers used with the cobalt chelating-Sepharose columns is critical to this invention because high salt, preferably 0.50M sodium chloride, minimizes non-specific electrostatic interaction as well as enhances active IL-4 binding to the metal chelating Sepharose. The concentration enables the IL-4 to be more selectively adsorbed to the cobalt chelating Sepharose column than impurities in the cell culture medium.

The following Examples illustrate the preferred embodiments of this invention.

EXAMPLE 1

PREPARATION OF S-SEPHAROSE ® FAST FLOW COLUMN

Prepare two cation exchange columns with S-Sepharose ® Fast Flow cation exchange resin in a buffer of 20 mM sodium phosphate, pH 7.2, and 0.12M NaCl. The first column is 1.5 L gel in a column, 100 mm in diameter and 45 cm in height and the second column is 0.25 L gel in a column, 50 mm in diameter and 300 mm in height. The smaller column has 15% of the bed volume of the larger column when each column is fully charged with the cation exchange gel. The columns are loaded as follows: Slurry S-Sepharose ® Fast Flow gel cation exchange resin in a buffer composed of 20 mM sodium phosphate, pH 7.2, and 0.12M NaCl. Pour the gel into the appropriate chromatography column, allow the liquid to flow or pump it through the bottom of the column.

Place a top flow adapter on the column and equilibrate the gel with 5 bed volumes of a buffer composed of 20 mM sodium phosphate, pH 7.2, 0.12M NaCl, by pumping the buffer through the column at a linear velocity of approximately 1 cm/min. Adjust the top flow adapter to press firmly on top of the resin bed. Then pump at least 5 bed volumes of a buffer composed of 20 mM sodium phosphate, pH 7.2, 0.12M NaCl, through the column at a linear velocity of approximately 1 cm/min and if necessary continue pumping the buffer through the column at the same flow rate until the pH of the effluent is between 7.1 and 7.3. Adjust the bed volumes of the columns so the smaller column has 15% the bed volume of the larger column.

EXAMPLE 2

PREPARATION OF COBALT CHELATING-SEPHAROSE ® FAST FLOW

Suspend chelating Sepharose ® Fast Flow gel in 5 volumes of 0.02M cobalt acetate and let stand overnight with occasional stirring. Wash the gel on a Buchner funnel with deionized water, then wash the gel with a buffer of 0.02M sodium phosphate, pH 7.2, containing 0.5M NaCl. Then slurry the gel in 0.5 gel volumes of 0.02M sodium phosphate buffer at pH 7.2, containing 0.5M NaCl. Pour 190 mL of the cobalt charged gel into a column 50 mm in diameter and 300 mm in height and pump the liquid through the column. Place a top flow adapter on the column and equilibrate the gel by pumping 0.02M sodium phosphate buffer at pH 7.2, containing 0.5M NaCl through the column at approximately 1 cm/min. Place a flow adapter on top of the column.

EXAMPLE 3

PREPARATION OF CHELATING SEPHAROSE ®FAST FLOW (NOT TREATED WITH A METAL SALT)

Slurry Chelating Sepharose ®Fast Flow gel in a buffer composed of 20 mM sodium phosphate at pH 7.2 with 0.5M NaCl. Pour 75 mL of the gel into the chromatography column from Example 2 so that the gel not treated with the metal salt settles in a uniform layer on the top of the cobalt charged gel. Place a flow adaptor on the column and equilibrate the gel with 0.02M sodium phosphate buffer at pH 7.2 containing 0.5M NaCl.

EXAMPLE 4

EQUILIBRATION OF COBALT CHELATING-SEPHAROSE ® COLUMN

After the cobalt chelating Sepharose ® Fast Flow and the untreated chelating Sepharose ®column is prepared according to Examples 2 and 3, invert the column so the cobalt treated resin is on top of the untreated resin. Continue pumping the buffer, i.e. 0.02M sodium phosphate, pH 7.2, 0.5M NaCl, through the column until the pH of the effluent is between 7.1 and 7.3.

EXAMPLE 5

PREPARATION OF SEPHACRYL ®S-200 HR COLUMN

Pump at least 1 bed volume of a buffer composed of 10 mM sodium citrate, pH 4.5, through the 1.8 L S-200 HR gel in a chromatography column, 50 mm diameter, 100 cm height, at a linear velocity of approximately 0.2 cm/min to equilibrate the column.

EXAMPLE 6

PREPARATION OF BUFFERS (a) 0.02M Sodium Phosphate, pH 7.2, 0.12M Sodium Chloride Mix together in deionized water 2.78 g/L sodium phosphate monobasic monohydrate, 7.03 g/L sodium chloride and sufficient amount of 6.3N sodium hydroxide to adjust the pH to 7.2 ($\pm$0.1).

(b) 0.02M Sodium Phosphate, pH 7.2, 0.26M Sodium Chloride.

Mix together in deionized water 2.78 g/L sodium phosphate monobasic monohydrate and 15.19 g/L sodium chloride. Adjust the pH to 7.2 ($\pm$0.1) with 6.3N sodium hydroxide.

(c) 0.02M Sodium Phosphate, pH 7.2, 0.50M Sodium Chloride

Mix together in deionized water 2.78 g/L sodium phosphate monobasic monohydrate, 29.22 g/L sodium chloride and sufficient amount of 50% NaOH to adjust the pH to 7.2 ($\pm$0.1).

(d) 0.02M Sodium Phosphate, pH 6.0, 0.5M Sodium Chloride

Mix together in deionized water 2.78 gm/L sodium phosphate monobasic monohydrate and 29.22 g/L sodium chloride. Adjust the pH to 6.0 ($\pm$0.1) with 6.3N sodium hydroxide/4N HCl.

(e) 10 mM Sodium Citrate, pH 4.5

Mix 210 grams (2.1 g/L) citric acid monohydrate with 100 L deionized water until the citric acid monohydrate is dissolved. Adjust the pH of the buffer to 4.5 with 4N hydrochloric acid and 6.3N sodium hydroxide, if needed. This buffer is used for diafiltration and ultrafiltration as well as for gel filtration chromatography.

(f) 20 mM Sodium Phosphate, pH 7.2

Mix 278 grams sodium phosphate monobasic monohydrate with 100 L deionized water and agitate until dissolved. Adjust the pH of the buffer to pH 7.2 with 50% NaOH and to a conductivity of 2–4 mS.

(g) 0.02M Sodium Phosphate, pH 6.0, 0.05M EDTA, 0.5M Sodium Chloride

Mix together in deionized water 2.78 gm/L sodium phosphate monobasic monohydrate and 19 g/L tetrasodium EDTA and 29.22 g/L sodium chloride. Adjust the pH to 6.0 ($\pm$0.1) with 6.3N sodium hydroxide/4N HCl.

EXAMPLE 7

CATION EXCHANGE CHROMATOGRAPHY TREATMENT OF CRUDE IL-4 SOLUTION

Adjust the crude IL-4 containing cell culture medium (total protein about 14,000 g) to pH 7.2 ($\pm$0.1) and adjust its conductivity to 14 mS ($\pm$1). Pump the solution through the S-Sepharose ® cation exchange column at a linear velocity of approximately 1.0 cm/min or less. Wash the column with the buffer prepared in Example 6(a). Isocratically elute the column with the buffer prepared in Example 6(b) at a linear velocity of approximately 0.2 cm/min. Collect the fractions which contain active IL-4 as determined by the SDS-PAGE and protein assays and pool them. The purity of the pooled active IL-4 is about 50%.

EXAMPLE 8

GRADIENT ELUTION OF PARTIALLY PURIFIED ACTIVE IL-4 SOLUTION ON CATION EXCHANGE COLUMN

Adjust the pH of the pooled active IL-4 solution made according to Example 7 to 7.2 ($\pm$0.1) with either 4N HCl or 6.3N NaOH as required. Adjust the conductivity of the solution with the buffer prepared in Example 6(f) to 14 mS ($\pm$1).

Pump the solution through an S-Sepharose ® column as prepared in Example 1 at linear velocity of approximately 1 cm/min or less. Collect the flow-through solution in one fraction.

Elute the column using a gradient of approximately 1.75 mS per bed volume and a linear flow rate of approximately 0.2 cm/min.

The low salt buffer used in the gradient is that made in Example 6(a), and the high salt buffer used in the gradient is that made in Example 6(c).

Collect 5 large fractions, each with a volume of approximately 0.5 bed volumes. Collect the remaining fractions (about 40–50) in volumes of 0.1 bed volumes.

Analyze the fractions for active IL-4 by the SDS-PAGE and protein assays. Pool the active IL-4 fractions. The purity of the pooled active IL-4 solution is about 60% to 70%.

EXAMPLE 9

COBALT CHELATING SEPHAROSE ® CHROMATOGRAPHY PURIFICATION OF ACTIVE RECOMBINANT HUMAN INTERLEUKIN-4

Adjust the pH of the IL-4 solution from Example 8 to 7.2 ($\pm$0.1) with 4N HCl and/or 6.3N sodium chloride. Adjust the conductivity of the solution to 45–50 mS.

Clarify the solution if necessary by centrifugation or microfiltration. Pump the solution (about 3.3 mg protein per mL gel) through the cobalt chelating Sepharose ® Fast Flow and untreated chelating Sepharose ® Fast Flow columns as prepared in Example 4 at a linear velocity of approximately 0.5 cm/min. Collect the flow-through in one fraction.

Wash the columns with approximately 10 bed volumes of the buffer prepared in Example 6(c) at a linear velocity of approximately 0.5 cm/min and collect the wash in no more than 5 fractions, then elute the column with approximately 10 bed volumes of the buffer made in Example 6(d) at a linear velocity of approximately 0.5 cm/min. Collect fractions with a volume of approximately 0.2 bed volumes. Analyze each sample for active IL-4 with SDS-PAGE and protein assays and pool the active IL-4 fractions.

The purity of the active IL-4 solution treated according to this Example 9 is about 90–95%.

EXAMPLE 10

ULTRAFILTRATION AND CONCENTRATION

Concentrate the pooled fractions from Example 9 using an Amicon stirred chamber fitted with a YM-10 membrane by placing the pooled fractions from Example 9 containing active human IL-4 in a container and adding approximately 0.25 volumes of the buffer prepared in Example 6(g). Concentrate the volume to approximately 0.2 the original volume by ultrafiltration on the YM-10 membrane. Dilute the concentrated retentate with 4 volumes of the buffer prepared in Example 6(e) and concentrate it to approximately 0.2 volumes by ultrafiltration on the YM-10 membrane.

The concentration step can be repeated to achieve approximately 0.1 the volume of the initial pooled fractions. Transfer the concentrate to an appropriate container and hold at cold room temperature for immediate use or store frozen at −20° C.

EXAMPLE 11

GEL FILTRATION CHROMATOGRAPHY (SIZE EXCLUSION)

Equilibrate a Sephacryl ® S-200 HR column with the buffer prepared in Example 6(e) by pumping at least one bed volume of the buffer through the column at a linear velocity of approximately 0.2 cm/min.

Clarify the solution made in Example 10 by centrifugation on a laboratory centrifuge at 4500 rpm for 30 minutes at 2° C.–6° C. Measure the $A_{280}$ and dilute the solution with the buffer prepared in Example 6(e) so there are 5 optical density units at 280 nm per mL.

Pump the resulting solution onto a Sephacryl ® S-200 HR column at a linear velocity of approximately 0.1 cm/min. Continue pumping the buffered of Example 6(e) through the column at a flow rate of approximately 0.1 cm/min. Collect one large fraction having a total volume of 0.4 to 0.55 bed volume, then collect 50 fractions of approximately 0.01 bed volume.

Select the fractions with the active IL-4 as determined by SDS-PAGE and protein assay. Pool the active IL-4 fractions and filter through a 0.2 micron sterile filter. Recover the filtrates which are 95% to 99% pure active IL-4 solutions as evidenced by the SDS-PAGE assay. The overall yield based on the active IL-4 in the cell culture medium is 70%.

All the assays used to determine the active fractions of interleukin-4 are conventional. For UV absorbance at 280 nm measurement of purified IL-4, 1.0 $A_{280}$ Optical Density Unit (OD) is equivalent to 1.6 mg by amino acid composition analysis and to 2.0 mg by Lowry's Method.

SDS-PAGE assay is also required for selecting active fractions. This method is discussed in Laemmli, U. K., Nature, 227: 680 (1970).

Lowry's Method is described in Lowry et al., J. Biol. Chem. 193, 265–275 (1951).

We claim:

1. A process for purifying a crude solution of active recombinant human interleukin-4 expressed from CHO-cell lines, comprising (a) charging said crude solution of active IL-4 buffered at a neutral to slightly alkaline pH and 13 to 15 mS to cation exchange chromatography on a crosslinked agarose gel matrix column to selectively bind the active recombinant human interleukin-4 to the column, washing with an equilibration buffer and isocratically eluting the active IL-4 from the column;

(b) charging the active human IL-4 solution from (a) in a buffer to chromatography on a smaller cation exchange column having about 15% the bed volume of the cation exchange column in (a), washing with an equilibration buffer, gradient eluting the bound active IL-4 from the column with a buffer system at pH 7.2, containing 0.12–0.50M sodium chloride and pooling the active eluates;

(c) adjusting the pH of the eluate pool to pH 7.2 and the conductivity to 45–50 mS, then charging the pooled eluates to a metal chelating agarose gel column in a buffer at about pH 6.7 to 8 and containing about 0.5M sodium chloride, then washing the column with a buffer at near neutral pH containing 0.5M sodium chloride, then isocratically eluting the active IL-4 with a buffer at pH 6.0 containing 0.50M sodium chloride;

(d) concentrating and diafiltrating the eluate from (c) at pH 4.5 on a stirred cell membrane that allows matter of less than 10,000 molecular weight to pass;

(e) charging the concentrate from (d) to size exclusion chromatography column on a crosslinked copolymer gel of allyldextran and N,N'-methylene bisacrylamide equilibrated with a buffer system at pH 4.5; and (f) collecting the purified solution of active recombinant human interleukin-4.

2. The process of claim 1 wherein in step (a) the equilibration buffer is 20 mM sodium phosphate at pH 7.2, containing 0.12M sodium chloride concentration.

3. The process of claim 1 wherein in step (b) the eluting buffer is a 20 mM sodium phosphate at pH 7.2 having 0.12–0.50M sodium chloride gradient therein.

4. The process of claim 1 wherein in step (b) the metal chelating gel column is a cobalt chelating agarose gel.

5. The process of claim 1 wherein in step (c) the eluting buffer is a 20 mM phosphate buffer at pH 6.0 containing 0.50M sodium chloride.

6. The process of claim 1 wherein the concentration of step (d) is accomplished by diafiltration against 20 mM sodium phosphate, 50 mM ethylene diamine tetraacetic acid, 0.5M sodium chloride at pH 6.0, and 10 mM citrate buffer at pH 4.5 to a concentration of up to 20 mg/mL.

7. The process of claim 1 wherein in step (e) the column is equilibrated with 10 mM sodium citrate.

* * * * *